US006344193B1

(12) United States Patent
Hammock et al.

(10) Patent No.: US 6,344,193 B1
(45) Date of Patent: Feb. 5, 2002

(54) INSECT CONTROL METHOD WITH GENETICALLY ENGINEERED BIOPESTICIDES

(75) Inventors: Bruce D. Hammock, Davis, CA (US); Billy Fred McCutchen, Wilmington, DE (US)

(73) Assignee: The Regents of The University of California, Oakland, CA (US)

( * ) Notice: Subject to any disclaimer, the term of this patent is extended or adjusted under 35 U.S.C. 154(b) by 0 days.

(21) Appl. No.: 09/206,766

(22) Filed: Jan. 15, 1998

Related U.S. Application Data

(63) Continuation of application No. 08/679,185, filed on Jul. 12, 1996, now abandoned, which is a continuation of application No. 08/270,956, filed on Jul. 5, 1994, now abandoned.

(51) Int. Cl.$^7$ .......................... A01N 63/00; A01N 43/40
(52) U.S. Cl. ...................... 424/93.2; 424/93.6; 514/319; 514/320
(58) Field of Search ................................. 504/116, 117; 424/93.1, 93.2, 93.6; 435/235; 514/319, 320

(56) References Cited

U.S. PATENT DOCUMENTS

| 4,668,511 A | * | 5/1987 | Aspirot et al. ................. 424/93 |
| 4,745,051 A | | 5/1988 | Smith et al. ................ 435/69.1 |
| 4,762,547 A | | 8/1988 | Iwasaki et al. ................ 424/93 |
| 4,870,023 A | | 9/1989 | Fraser et al. ............. 435/235.1 |
| 4,888,340 A | * | 12/1989 | Neh et al. .................... 514/403 |
| 4,929,718 A | | 5/1990 | Possani et al. ................ 424/93 |
| 5,071,748 A | | 12/1991 | Miller .......................... 424/93 |
| 5,098,706 A | | 3/1992 | Hammock et al. ............. 424/93 |
| 5,162,308 A | * | 11/1992 | Brown et al. .................. 514/63 |
| 5,177,308 A | | 1/1993 | Barton et al. ................ 800/205 |
| 5,180,581 A | | 1/1993 | Miller et al. .................. 424/93 |
| 5,238,724 A | * | 8/1993 | Bjostad et al. ................. 424/84 |
| 5,266,314 A | | 11/1993 | Maeda ......................... 424/93 |
| 5,266,317 A | | 11/1993 | Tomalski et al. ............. 424/93 |
| 5,328,915 A | * | 7/1994 | Long et al. .................. 514/310 |
| 5,770,192 A | | 6/1998 | Cayley et al. ............. 424/93.2 |

FOREIGN PATENT DOCUMENTS

| EP | 0225777 | 6/1987 |
| EP | 0505207 | 3/1992 |
| WO | 95/05741 | 2/1995 |
| WO | 96/03048 | 8/1996 |

OTHER PUBLICATIONS

Stewart et al. Nature 352:85–88, 1991.*
McCutchen et al. Bio/Technology 9:848–852, 1991.*
Pike et al. J Ecom. Entomol. 86:586–593, 1993.*
Hammock et al., "The Role of Juvenile Hormone Metabolism in the Metamorphosis of Selected Lepidoptera," Chemical Abstracts, 102 (1985), entry 76006b.

Abdel–Aal and Hammock, "3–Octylthio–1,1,1–trifluoro–2–propanone, A High Affinity and Slow Binding Inhibitor of Juvenile Hormone Esterase from *Trichoplusia ni* (Hüber)," *Insect Biochem.*, 15:1 (1985), pp. 111–122.

Abdel–Aal and Hammock, "Transition State Analogs as Ligands for Affinity Purification of Juvenile Hormone Esterase," *Science*, 233 (Sep. 1986), pp. 1073–1076.

Bachmair and Varshavsky, "The Degradation Signal in a Short–Lived Protein," *Cell*, 56 (Mar. 1989), pp. 1019–1032.

Cheung and Hammock, "Micro–Lipid–Droplet Encapsulation of *Bacillus thuringiensis* subsp. *israelensis* δ–Endotoxin for Control of Mosquito Larvae," *Appl. & Environ. Microbiol.*, 50:4 (Oct. 1985), pp. 984–988.

Chiang and Dice, "Peptide Sequences that Target Proteins for Enhanced Degradation During Serum Withdrawal," *J. of Biol. Chem.*, 263:14 (May 1988), pp. 6797–6805.

Hammock and Sparks, "A Rapid Assay for Insect Juvenile Hormone Esterase Activity," *Analytical Biochemistry*, 82 (1977), pp. 573–579.

Hammock et al., "Expression and Effects of the Juvenile Hormone Esterase in a Baculovirus Vector," *Nature*, 344:6265 (Mar. 1990), pp. 458–461.

Hammock and Rose, "Analysis of Juvenile Hormone Esterase Activity," Chpt. 32, pp. 487–495 in Law et al. (Eds.), *Methods in Enzymology*, vol. III: *Steroids and Isoprenoids* (Part B), Academic Press (1985).

Hammock et al., "Trifluoromethylketones as Possible Transition State Analog Inhibitors of Juvenile Hormone Esterase," *Pesticide Biochem. & Physiology*, 17 (1982), pp. 76–88.

Hammock et al., "Selective Inhibition of JH Esterases from Cockroach Hemolymph," *Pesticide Biochem. & Physiology*, 7 (1977), pp. 517–530.

Hammock et al., "Strategies for the Discovery of Insect Control Agents: . . ." Chpt. 12 in Steffens et al. (Eds), *Biomechanism Regulating Growth & Development*, USDA Beltsville Symp. vol. 12, Kluwer Academic Press (1988).

Hanzlik et al., "Isolation and Sequencing of cDNA Clones Coding for Juvenile Hormone Esterase from *Heliothis virescens*," *J. of Biol. Chem.*, 264:21 (Jul. 1989), pp. 12419–12425.

(List continued on next page.)

*Primary Examiner*—Dave T. Nguyen
*Assistant Examiner*—Ram R. Shukla
(74) *Attorney, Agent, or Firm*—Knobbe, Martens, Olson & Bear, LLP

(57) ABSTRACT

Insect pests can be controlled by treating the pests or their loci with a combination of recombinant virus and organic insecticide. The recombinant virus preferably is a baculovirus. Combinations of recombinant baculovirus with chemical insecticides provide a dose-response in pests, such as insects, that is greater than additive. Preferred treatments of the invention are uses of recombinant baculoviruses that express a foreign protein or toxin, with pyrethroid insecticides. Treatments against pyrethroid resistant pests are especially useful.

13 Claims, 1 Drawing Sheet

OTHER PUBLICATIONS

Hanzlik and Hammock, "Characterization of Affinity–purified Juvenile Hormone Esterase from *Trichoplusia ni,*" *J. Biol. Chem.*, 1987:23 (Oct. 1987), pp. 12584–13591.

Huynh et al., "Constructing and Screening cDNA Libraries in λgt10 and λgt11," Chtp. 2, IRL Press (Oxford), (1985), pp. 49–78.

Ichinose et al., Pharmacokinetic Studies of the Recombinant Juvenile Hormone Esterase in *Manduca sexta, Pesticide Biochem. & Physiology*, 42 (1992), pp. 13–23.

Ichinose eta l., "Uptake of Juvenile Hormone Esterase by Pericardial Cells of *Manduca sexta,*" submitted to *Insect Biochem. Molec. Biol.* (1992).

Carbonell et al., "Baculovirus Interaction with Nontarget Organisms: a Virus–Borne Reporter Gene is Not Expressed in Two Mammalian Cell Lines," *Appl. Environ. Microbiol.*, 53:7 (Jul. 1987), pp. 1412–1417.

Philpott and Hammock, "Juvenile Hormone Esterase is a Biochemical Anti–Juvenile Hormone Agent," *Insect Biochem.*, 20:5 (1990), pp. 451–459.

Rogers et al., "Amino Acid Sequences Common to Rapidly Degraded Proteins: The PEST Hypothesis," *Science*, 234 (Oct. 1986), pp. 364–368.

Sparks and Hammock, "Induction and Regulation of Juvenile Hormone Esterases During the Last Larval Instar of the Cabbage Looper, *Trichoplusia ni,*" *J. Insect. Physiolo.*, 25 (1979), pp. 551–560.

Sparks and Hammock, "Comparative Inhibition of the Juvenile Hormone Esterases from *Trichoplusia ni, Tenebrio molitor,* and *Musca domestica,*" *Pesticide Biochem. & Physiology*, 14 (1980), pp. 290–302.

Wozniak and Jones, "Immunochemical Characterization of Juvenile Hormone Esterase from Different Species of Lepidoptera," *Biochem. & Biophys. Res. Commun.*, 144:3 (May 1987), pp. 1281–1286.

Wroblewski et al., "Regulation of Juvenile Hormone Esterase Gene Expression in the Tobacco Budworm (*Heliothis virescens*)," *Archives of Biochem. & Biophys.*, 278:2 (May 1990), pp. 461–466.

Eldridge et al., "Insecticidal Properties of Genetically Engineered Baculoviruses Expressing an Insect Juvenile Hormone Esterase Gene," *Appl. & Environ. Microbiol.*, 58:5 (May 1992), pp. 1583–1591.

Hayakawa, "Structure of a Growth–Blocking Peptide Present in Parasitized Insect Hemolymph," *J. of Biol. Chem.*, 266:13 (May 5, 1991), pp. 7982–7984.

Hayakawa, "A Putative New Juvenile Peptide Hormone in Lepidopteran Insects," *Biochemical and Biophysical Research Communications*, 185:3 (Jun. 30, 1993), pp. 1141–1147.

Smith et al., "Prodction of Human Beta Interferon in Insect Cells Infected with a Baculovirus Expression Vector," *Mol. Cell. Biol.*, 3 (1983), pp. 2156–2165.

Betana et al., "Potential of Baculo Viruses Expressing a Scorpion Toxin and an Esterase in Agriculture . . . ," *Abstr. Pap. Am. Chem. Soc.*, (206 Meet., Pt. 1, AGR0122), 1993 (Abstract only).

Hayakawa, "Juvenile Hormone Esterase Activity Repressive Factor in the Plasma of Parasitized Insect Larvae," *J. Biol. Chem.*, 265:19 (1990), pp. 10812–10816.

Hayakawa, "Juvenile Hormone Esterase Activity Repressive Peptide in the Parasitized Armyworm Hemolymph," *Zool. Sci.* (Tokyo), 7:6 (1990), p. 1061 (Abstract only).

Ward et al., "Analysis of the Catalytic Mechanism of Juvenile Hormone Esterase by Site–Directed Mutagenesis," *Int. J. Biochem.* (England), 24:12 (Dec. 1993), pp. 1933–1941 (Abstract only).

Hammock et al., "Development of Recombinant Viral Insecticides by Expression of an Insect–Speicfic Toxin . . . ," *Arch. Insect Biochem. Physiol.* (US), 22:3–4 (1993), pp. 315–344 (Abstract only).

Possee et al., "Expression of the Proteins with Insecticidal Activities Using Baculov Virus Vectors . . . ," *Ann. N.Y. Acad. Sci.*, 646 (1991), pp. 234–239 (Abstract only).

Hammock et al., "Improving the Efficacy of Baculo Virus Insecticides by Expressing with Insect Selective Proteins," *Abstr. Pap. Am. Chem. Soc.* (202 Meet., Pt. 1, AGR09) (1991) (Abstract only).

Bonning et al., "Further Development of a Recombinant Baculovirus Insecticides Expressing the Enzyme JHE from Heliothis–Virescens," *Biochem. Mol. Biol.*, 22:5 (1992) pp. 453–458 (Abstract only).

Cameron et al., "Insect Cell Culture Technology in Baculovirus Expression Systems," *Trends in Biotechnology*, vol. 7 (1989), pp. 66–70.

Jones and Hammock, "Prepupal Regulation of Juvenile Hormone Esterase through Direct Induction by Juvenile Hormone," *J. Insect Physiol.*, 29:6, (1983), pp. 471–475.

Sparks and Hammock, "A Comparison of the Induced and Naturally Occurring Juvenile Hormone Esterases from Last Instar Larvae of *Trichoplusia ni*," *Insect Biochem.*, 9, (1979), pp. 411–421.

Sparks et al., Effects of the Anti Hormone–Hormone Mimic ETB on the Inductio nof Insect Juvenile Hormone Esterase in *Trichoplusia ni, Life Sci.*, 25 (1979), pp. 445–450.

Zlotkin et al., "The Effect of Scorpion Venom on Blowfly Larvae—A New Method for the Evaluation of Scorpion Venoms Potency," *Toxicon*, 9 (1971), pp. 1–8.

Zlotkin et al., "An Excitatory and a Depressant Insect Toxin from Scorpion Venom both Affect Sodium Conductance and Possess a Common Binding Stie," *Arch. Biochem. & Biophys.*, 240:2 (Aug. 1985), pp. 877–887.

Hammock, "Regulation of Juvenile Hormone Titer: Degradation," in *Comprehensive Insect Physiology, Biochemistry, and Pharmacology* (Kerkut and Gilbert, eds.) Pergamon Press (1985), pp. 431–472.

Harshman et al., "Effects of Recombinant Juvenile Hormone Esterase on *Aedes aegypti,*" *Proc. Calif. Mosq. Vector Control Assoc.*, (1991), pp. 77–80.

Booth et al., Localization of JHE During Development in Normal and in Recombinant Baculovirus–Infected Larvae of the Moth *Trichoplusia ni, Tissue & Cell*, 24:2 (1992), pp. 267–282.

McCutchen et al., "Development of Surrogate Substrates for Juvenile Hormone Esterase," *Archives of Biochemistry and Biophysics*, 307:2 (Dec. 1993), pp. 231–241.

Abdel–Aal and Hammock, "Apparent Multiple Catalytic Sites Involved in the Ester Hydrolysis of Juvenile Hormones by the Hemolymph and . . . ," *Arch. Biochem. Biophys.*, 243:1, (1985), pp. 206–219.

Roelvink et al., "Dissimilar Expression of *Autographa californica* Multiple Nucleocapsid Nuclear Polyhedrosis Virus Polyhedrin and p10 Gene," *J. Gen. Virol.*, 73 (1992), pp. 1481–1489.

Touhara et al., "Ligand Binding by a Recombinant Insect Juvenile Hormone Binding Protein," *Biochem.*, 32:8 (1993), pp. 2068–2075.

McCutchen et al., "Recombinant Baculovirus Expressing an Insect–selective Neurotoxin: . . . ," in *Natural & Engineered Pest Management Agents* (Hedin et al., eds), ACS Sympo. Series #551, Am. Chem. Soc., (1994) pp. 348–367.

Heinz et al., "Direct Effects of Recombinant Nuclear Polyhedrosis Viruses on Selected Non–Target Organisms," *J. Econ. Entomol.*, 88:2, (1995), pp. 259–264.

Hammock, "Recombinant Baculoviruses as Biological Insecticides," in *Pest Management: Biologically Based Technologies* (Lumsden and Vaughn, eds.), ACS Symp. Series, Am. Chem. Soc., (1993), pp. 313–325.

Bonning and Hammock, "Lethal Ratios: An Optimized Strategy for Presentation of Bioassay Data Generated from Genetically Engineered Baculoviruses," *J. Invert. Pathol.*, 62 (1993), pp. 196–197.

Maeda et al., "Recombinant Baculoviruses Expressing Foreign Genes for . . . ," in *Pest Control with Enhanced Environmental Safety*, (Duke et al., eds.), ACS Sympos. Series #524, Am. Chem. Soc. (1993), pp. 281–297.

Bonning and Hammock, "Development and Potential of Genetically Engineered Viral Insecticides," *Biotechnol. Genetic Engeinnering Rev.*, 10 (1992), pp. 455–489.

Hammock et al., "Cloning, Expression and Biological Activity of the JHE from *Heliothis virescens*," in *Molecular Insect Science* (Hagedorn et al., eds.), Plenum Press (1990), pp. 49–56.

Bonning et al., "Superior Expression of JHE and β–Galactosidase from the Basic Protein Promoter of *Autographa californica* Nuclear Polyhedrosis Virus Compared to the . . . ," *J. Gen. Virol.*, 75 (1994), pp. 1551–156.

Harshman et al., "Cloning, Characterization and Genetics of the JHE Gene from *Heliothis virescens*," *Insect. Biochem. Molec. Biol.*, 24:7 (1994), pp. 671–676.

Ichinose et al., "Pharmacokinetics and Tissue Uptake of the Recombinant JHE in Insects" in *Pesticides/Environment*: . . . , (Mitsui et al., eds.), Proc. of 1st Int'l. Symp. on Pest. Sci., Pesticide Sci. Soc. of JP (1993).

Bonning et al., "Insect Control by Use of Recombinant Baculoviruses Expressing JHE," in Natural and Engineered Pest Management Agents (Hedin et al., eds.), ACS Symp. Ser. #551, Am. Chem. Soc. (1994), pp. 368–383.

Luttrell et al., "Laboratory and Filed Studies on the Efficacy of Selected Chemical Insecticide–Elear (*Baculovirus heliothis*) Combinations Against Heliothis spp.," *Journal of Economic Entomology*, 72:1, pp. 57–59 (1979).

Abstract of R.P. Jacques, "Field Test on Control of the Imported Cabbageworm Lepidoptera Pieridae and the Cabbage Looper Lepidoptera Noctuidae by Mixtures of Microbial and Chemical Insecticides" (from *Can. Entomolo.*, 120:6, pp. 575–580), *Biological Abstracts*, 86, abstract No. 68459, 1988.

Abstract of Silvie et al., "Evaluation of a Virus–Insecticide Combination for Cotton Pests Control in Togo"(from *Crop Prot.*, 12:8, pp. 591–596, 1993), *Chemical Abstracts*, 120:19, (May 9, 1994).

Abstract of Chaudhari et al., "Effect of Insecticides on the Activity of Nuclear Polyhedrosis Virus of *Spodoptera litura* (Fabricus) in Laboratory Bioassay Tests" (from *J. Entomol. Res.*, 7:2, pp. 173–179, 1983), *Chemical Abstracts*, 100:25 (Jun. 18, 1984).

Abstract of R.P. Jaques, "Tests on Microbial and Chemical Insecticides for Control of *Trichoplusia ni* and *Pieris rapae* on Cabbage," (from *Can. Entomol.*, 105:1, pp. 21–27, 1973), *Chemical Abstracts*, 78:19 (May 14, 1973).

Moffat, Anne Simon, "New Chemicals Seek to Outwit Insect Pests," *Science*, 261, pp. 550–551 (1993).

Zlotkin, "Toxins Derived from Arthropod Venoms Specifically Affecting Insects," Chapter 15 in *Comprehensive Insect Physiology, Biochemistry & Pharmacology*, vol. 10, pp. 499–541 (1985).

Piek et al., "The Pharmacology of Microbracon Venom," *Comp. Biochem. Physiol.*, vol. 72C, pp. 303–309 (1982).

Maeda, "Increased Insecticidal Effect by a Recombinant Baculovirus Carrying a Synthetic Diuretic Hormone Gene," *Biochemical and Biophysical Research Communications*, 165:3, pp. 1177–1183 (1989).

Miller et al., "Bacterial, Viral, and Fungal Insecticides," *Science*, 219, pp. 715–721, (Feb. 11, 1983).

Carbonell et al., "Synthesis of a Gene Coding for an Insecti–Specific Scorpion Neurotoxin and Attempts to Express it Using Baculovirus Vectors," *Gene*, 73, pp. 409–418 (1988).

Dee et al., "Expression and Secretion of a Functional Scorpion Insecticidal Toxin in Cultured Mouse Cells," *Bio/Technology*, 8, pp. 339–342, (Apr. 1990).

Gordon et al., "The Binding of the Insect Selective Neurotoxin (AaIT), from Scorpion Venom to Locust Synaptosomal Membranes," *Biochimica et Biophysica Acta*, 778, pp. 349–358 (1984).

Sakurai et al., "Complete Nucleotide Sequence of Gene for Sex–Specific Storage Protein of *Bombyx mori*," *Nucleic Acids Research*, 16:15, pp. 7717–7718 (1988).

Adachi et al., "cDNA Structure and Expression of Bombyxin, an Insulin–like Brain Secretory Peptide of the Silkmoth *Bombyx mori*," *The Journal of Biological Chemistry*, 264:13, pp. 7681–7685, (May 5, 1989).

Merryweather et al., "Construction of Genetically Engineered Baculovirus Insecticides Containing the *Bacillus thuringiensis* subsp. kurstaki HD–73 Delta Endotoxin," *Journal of General Virology*, 71, pp. 1535–1544 (1990).

Martens et al., "Insecticidal Activity of a Bacterial Crystal Protein Expressed by a Recombinant Baculovirus in Insect Cells," *Applied and Environmental Microbiology*, 56:9, pp. 2764–2770, (Sep. 1990).

Tomalski and Miller, "Insect Paralysis by Baculovirus–Mediated Expression of a Mite Neurotoxin Gene," *Nature*, 352, pp. 82–85, (Jul. 4, 1991).

McCutchen et al., "Development of a Recombinant Baculovirus Expressing an Insect–Selective Neurotoxin: Potential for Pest Control," *Bio/Technology*, 9, pp. 848–852, (Sep. 1991).

Maeda et al., "Insecticidal Effects of an Insect–Specific Neurotoxin Expressed by a Recombinant Baculovirus," *Virology*, 184, pp. 77–780, (1991).

Stewart et al., "Construction of an Improved Baculovirus Insecticide Containing an Insect–Specific Toxin Gene," *Nature*, 352, pp. 85–88, (Jul. 4, 1991).

Watson et al., 1987, in: *Molecular Biology Of The Gene*, Fourth Edition, Benjamin/Cummings Publishing Co., Menlo Park, CA, p. 313.

*Webster's II New Riverside University Dictionary*, (Soukhanov et al., eds.), 1984, Houghton Mifflin Co., Boston, MA, p. 67.

Pike et al. 1993 J. Econ. Entomol. 86(2): 586–593.

Proc. Natl. Acad. Sci, USA vol. 90, pp. 338–3392, Apr. 1993, Plant Biology. Korth K. L. et al. Baculovirus expression of the maize mitochondrial protein URF–13 confers insecticidal activity in cell cultures and larvae.

Virology 1991 Oct.; 184(2): 777–80, Maeda S. et al. Insecticidal effects of an insect–specific neurotoxin expressed by a recombinant baculovirus.

* cited by examiner

FIG. 1

| IA | IIA | IIIA |
| IB | IIB | IIIB |
| CONTROL | WTAcNPV | AcAaIT |

INSECT CONTROL METHOD WITH GENETICALLY ENGINEERED BIOPESTICIDES

This is a continuation of application Ser. No. 08/679,185, filed Jul. 12, 1996, now abandoned, which was a continuation of application Ser. No. 08/270,956, filed Jul. 5, 1994, now abandoned.

FIELD OF THE INVENTION

The present invention generally relates to uses of recombinant expression vectors expressing foreign proteins in controlling insects, and more particularly to a method utilizing insect pathogens, preferably recombinant, in conjunction with synthetic chemical insecticides to magnify insect kill rate.

This invention was made with Government support under Grant No. 5-T32-ES07059, awarded by the National Institutes of Health. The Government has certain rights in this invention.

BACKGROUND OF THE INVENTION

The lepidopteran family Noctuidae includes some of the most destructive agricultural pests, such as the genera Heliothis, Heliocoverpa, Spodoptera, and Trichoplusia. For example, included in this family are the tobacco budworm (*Heliothis virescens*), the cotton bollworm (*Heliocoverpa zea*), the cotton leafworm (*Alabama argillacea*), the spotted cutworm (*Amathes c-nigrum*), the glassy cutworm (*Crymodes devastator*), the bronzed cutworm (*Nephelodes emmedonia*), the fall armyworm (*Laphygma frugiperda*), the beet armyworm (*Spodoptera exigua*), and the variegated cutworm (*Peridroma saucia*). Attempts to control these and other insects have often involved the use of pyrethroid insecticides. Wildtype baculoviruses have been used with limited commercial success.

Pyrethroid insecticides now dominate the insecticide market with sales reaching into the billions annually. However, sales are beginning to stalemate due in part to the wide-scale presence of pest resistance to these compounds. In cotton alone, the presence of pyr-R Heliothis species has begun to result in millions of lost dollars annually. In fact, in several cases pyrethroid insecticides have completely failed to control infestations of Heliothis larvae in cotton, which has resulted in complete destruction of the crop. Consequently, there has been an enormous effort to control pyrethroid resistance in Heliothis species in cotton.

Agricultural producers sometimes attempt to restrain their use of pyrethroid insecticides until late in the growing season as a strategy against pyrethroid resistance. As a result, the producers have to turn to the less effective and more expensive organophosphate and carbamate insecticides, which have also been plagued with resistance problems. Therefore, the development of a new and effective pesticide to control pyr-R pests would be extremely valuable in any management strategy.

Resistance of agricultural pests to pesticides also leads to environmental and human health risks. These problems arise because another response by producers to pyrethroid (and other insecticide) resistance is the use of increasing amounts of pesticide, and the use of more non-selective and toxic compounds, in order to overcome pest resistance. This creates a destructive and vicious cycle.

Nevertheless, the uses of synthetic chemicals, such as exemplified by the pyrethroids, are an integral component of modern agriculture and are probably necessary to maintain our current level of agriculture productivity, although alternative control agents, such as the earlier mentioned recombinant insect pathogens, are being explored for pest control.

Recently, the nuclear polyhedrosis virus *Autograipha californica* (AcNPV), from the family Baculoviridae, has been genetically modified for an increased speed of kill by expressing insect-selective toxins. The introduction of insect-selective toxins into an insect-pathogenic virus has resulted in an approximate 30% reduction in the killing time of insect hosts, as is described by U.S. Ser. No. 08/472,053, filed Jun. 6, 1995, which is a continuation-in-part of U.S. Ser. No. 08/229,417, filed Apr. 15, 1994, which is a continuation-in-part application of U.S. Ser. No. 07/629,603, filed Dec. 19, 1990, having (in part) common assignment herewith.

Among the insect specific toxins suggested for use in insect control are toxins from *Bacillus thuringiensis* from the scorpions *Buthus eupeus* and *Androctonus australis* and from the mite *Pyemotes tritici*. Further, Hammock et al., (*Nature*, 344, pp. 458–461, 1990) have described use of JHE to control insects, U.S. Ser. No. 08/440,520, filed May 12, 1995, U.S. Ser. No. 07/927,851, filed Aug. 10, 1992, and U.S. Pat. No. 5,098,706, issued Mar. 24, 1992, all of common assignment herewith.

A new tool to control resistant, as well as susceptible, insect pest populations would be very desirable.

SUMMARY OF THE INVENTION

In one aspect of the present invention, a method for controlling pests is provided. Pests controlled in accordance with the invention are, for example, from the group insects, acarids, and nematodes. Such pests are treated (or their loci treated) with a synergistic combination of recombinant virus and organic insecticide. The recombinant virus preferably is a baculovirus that expresses a foreign protein or a functional derivative thereof in pest cells infected with the recombinant baculovirus.

Treatments in accordance with the invention can be simultaneous (such as by applying a pre-mixed composition of recombinant virus and organic insecticide). Alternatively, the pests or loci may first be treated by applying virus followed by organic insecticide within about 24 hours.

BRIEF DESCRIPTION OF THE DRAWING

FIG. 1 illustrates "before and after" larval exposure pictures of tomato plants to illustrate a property of insect control in conjunction with the use of recombinant baculoviruses.

DETAILED DESCRIPTION OF THE PREFERRED EMBODIMENTS

The present invention is the use of genetically engineered insect viruses in combination with synthetic, chemical insecticides to treat pests such as insects. Although baculoviruses will be used throughout as an illustration, this invention can be practiced with a variety of insect viruses, including DNA and RNA viruses. Using baculovirus as one example of insect viruses, we have discovered an interaction between the use of recombinant viruses in conjunction with chemical insecticides that can have an effect greater than the single effects. We will first describe suitable recombinant baculoviruses for practicing the invention.

By "baculovirus" insecticides is meant any baculovirus of the family Baculoviridae, such as a nuclear polyhedrosis virus (NPV). Baculoviruses are a large group of evolutionarily related viruses, which infect only arthropods; indeed, some baculoviruses only infect insects that are pests of commercially important agricultural and forestry crops, while others are known that specifically infect other insect pests. Because baculoviruses infect only arthropods, they pose little or no risk to humans or the environment.

Of the suitable DNA viruses, in addition to the Baculoviridae are the entomopox viruses (EPV), such as *Melolontha melonotha* EPV, *Amsacta moorei* EPV, *Locusta migratoria* EPV, *Melanoplus sanguinipes* EPV, *Schistocerca gregaria* EPV, *Aedes aogypti* EPV, and *Chironomus luridus* EPV. Other suitable DNA viruses are granulosis viruses (GV). Suitable RNA viruses include togaviruses, flaviviruses, picornaviruses, cytoplasmic polyhedrosis viruses (CPv), and the like. The subfamily of double stranded DNA viruses Eubaculovirinae includes two genera, NPVs and GVs, which are particularly useful for biological control because they produce occlusion bodies in their life cycle. Examples of GVs include *Cydia pomonella* GV (coddling moth GV), *Pieris brassicae* GV, *Trichoplusia ni* GV, *Artogeia rapae* GV, and *Plodia interpunctella* GV (Indian meal moth).

Suitable baculoviruses for practicing this invention may be occluded or non-occluded. The nuclear polyhedrosis viruses ("NPV") are one baculovirus sub-group, which are "occluded." That is, a characteristic feature of the NPV group is that many virions are embedded in a crystalline protein matrix referred to as an "occlusion body." Examples of NPVs include *Lymantria dispar* NPV (gypsy moth NPV), *Autographa californica* MNPV, *Anagrapha falcifera* NPV (celery looper NPV), *Spodoptera litturalis* NPV, *Spodoptera frugiperda* NPV, *Heliothis armigera* NPV, *Mamestra brassicae* NPV, *Choristoneura fumiferana* NPV, *Trichoplusia ni* NPV, *Heliocoverpa zea* NPV, and *Rachiplusia ou* NPV. For field use occluded viruses are preferable due to their greater stability since the viral polyhedrin coat provides protection for the enclosed infectious nucleocapsids.

Among illustrative, useful baculoviruses in practicing this invention are those *Anagrapha falcifera, Anticarsia gemmatalis, Buzura suppressuria, Cydia pomonella, Heliocoverpa zea, Heliothis armigera, Manestia brassicae, Plutella xylostella, Spodoptera exigua, Spodoptera littoralis*, and *Spodoptera litura*. A particularly useful "NPV" baculovirus for practicing this invention is AcNPV, which is a nuclear polyhedrosis virus from *Autographa californica. Autographa californica* is of particular interest because various major pest species within the genera Spodoptera, Trichoplusia, and Heliothis are susceptible to this virus.

Such baculoviruses may be genetically engineered into more potent insecticidal forms by cloning genes encoding a foreign protein such as insect toxin into the genome of the baculovirus. Illustrative toxins are from the scorpions *Buthus eupeus* and *Androctonus australis* and from the mite *Pyemotes tritici*.

The expressed foreign protein (which may be a glycoprotein) preferably is an insecticidal toxin, particularly an arthropod or other invertebrate toxin, such as a scorpion toxin, a wasp toxin, a snail toxin, or a spider toxin. A useful scorpion toxin is, for example, that from *Androctonus australis*. A useful snail venom is that from the snail conotoxins (cone shell snail poisons), which the animal delivers by mouth and some individual toxins of which appear to be selective for arthropods including insects. See, for example, Olivera et al., "Diversity of Conus Neuropeptides," *Science*, 249:257–263 (1990).

The amino acid sequence of the excitatory toxin from *Androctonus australis* (AaIT), was determined and the sequence published in Darbon 1982. The AaIT toxin exhibits toxicity to insects, while being non-toxic to isopods and mammals.

Various other scorpion toxins such as of the Buthoid scorpion can also be used, such as LqqIT2, which is a depressive insect toxin from *Leiurus quinquestriatus* quinquestriatus. The purification method used to obtain this neurotoxin was published by Zlotkin et al., Archives of Biochem. Biophys., 240:877–887 (1985).

BjIT2 is another depressive insect toxin and is from *Buthotus judaicus*. The purification has been published in Lester et al., *Biochim. Biophys. Acta*, 701:370–381 (1982). BjIT2 exists in two isoforms which differ in amino acid sequence at position 15. Form 1 has isoleucine in this position while form 2 has valine.

LqhIT2 is yet another depressive insect toxin from *Leiurus quinquestriatus* hebraeus which was purified using reverse phase HPLC.

An "intermediate" toxin has also been discovered which affects insect sodium channels in a manner very similar to the effect of alpha toxins on mammalian sodium channels. This neurotoxin was derived from a yellow scorpion *Leiurus quinquestriatus* hebraeus, Buthinae, Buthidae and is called herein LqhP35. The identification and purification of this toxin was described in "Toxin to Insects Derived from the Venom of the Scorpion *Leiurus quinquestriatus* hebraeus," published by Citan et al., *Biochemistry*, 29:5941–5947 (1990), renamed "LqhαIT."

Other toxins, purified from the venom of the chactoid scorpion, *Scorpio maurus* palmatus, can also be used. For example, SmpIT2, from the chactoid scorpion, *Scorpio maurus* palmatus, is a depressive insect toxin. Its purification is described in Lazarovici et al., *J. Biol. Chem.*, 257:8397–8404 (1982).

Still other toxins purified from the venom of the chactoid scorpion, *Scorpio maurus* palmatus, are SmpCT2 and SmpCT3, and crustacean toxins, whose purification has been described in Lazarovici, Ph.D. thesis (1980), Hebrew University, Jerusalem, "Studies on the Composition and Action of the Venom of the Scorpion *Scorpio maurus* palmatus (Scorpionidae)."

For producing recombinant baculoviruses for the purpose of controlling insects, a secretion signal sequence is preferably included. Secretion signal sequences may be derived from proteins of bacteria, yeast, fungi, or higher eukaryotes, including both animals and plants (for examples, see Watson, *Nuci. Ac. Res.*, 12:5145–5164 (1984). More preferred are secretion signal sequences from proteins of insect origin, for example those of cecropin B from *Hyalophora cecropia* (van Hofsten et al., PNAS, 82:2240–2243 (1985)), and the eclosion hormone from *Manduca sexta* (Horodyski et al., PNAS, 86:8123–8127 (1989)). Also preferred are the secretion signal sequences naturally associated with scorpion toxins, which can be determined by the analysis of mRNA, cDNA, or genomic DNA. More preferred is the natural secretion signal sequence of AaIT (Bougis et al., *J. Biol. Chem.*, 264:19259–19265 (1989)).

Foreign proteins, or toxins, may be expressed as functional derivatives of the toxin. A "functional derivative" of the toxin is a compound which possesses a biological activity (either functional or structural) that is substantially similar to a biological activity of the toxin. The term "functional derivative" is intended to include the "fragments," "variants," "analogues," or "chemical derivatives" of a molecule. A "fragment" of a molecule such as the toxin is meant to refer to any polypeptide subset of the molecule. A "variant" of a molecule such as the toxin is meant to refer to a molecule substantially similar in structure and function to either the entire molecule, or to a fragment thereof. A molecule is said to be "substantially similar" to another molecule if both molecules have substantially similar structures or if both molecules possess a similar biological activity. Thus, provided that two molecules possess a similar activity, they are considered variants as that term is used herein even if the structure of one of the molecules is not found in the other, or if the sequence of amino acid residues is not identical. An "analog" of a molecule such as the toxin is meant to refer to a molecule substantially similar in function to either the entire molecule or to a fragment thereof. As used herein, a molecule is said to be a "chemical derivative" of another molecule when it contains additional chemical moieties not normally a part of the molecule.

Such moieties may improve the molecule's solubility, absorption, biological half-life, etc. Moieties capable of mediating such effects are disclosed in Remington's Pharmaceutical Sciences (1980). Procedures for coupling such moieties to a molecule are well known in the art.

Expression of the toxin will, in general, include a promoter region sufficient to direct the initiation of RNA synthesis. One baculovirus gene is that coding for polyhedrin, since the polyhedrin protein is one of the most highly expressed eucaryotic genes known. Thus, the polyhedrin promoter is preferred, although other promoter and hybrid promoter sequences may be used.

As will be further exemplified, a particular recombinant baculovirus has been constructed from *Autographa californica* by cloning a gene encoding the insect toxin from *Androctonous australis* (Hector) into the AcNPV genome, with the toxin being expressed under polyhedrin promoter control. (Such a construction is also described by U.S. Ser. No. 08/229,417, already referenced and *Bio/Technology*, 9:848–852, 1991.) We designate this particular, illustrative recombinant baculovirus embodiment as "AcAaIT," but note that some persons in the art have utilized the designation "IT," instead of "IT," for the toxin. (See, for example, Loret et al., *Biochemistry*, 29, pp. 1492–1501 (1990), who described several of the active neurotoxins from the scorpion as "*Androctonous australis* Hector.") We have used this recombinant baculovirus (such as in comparison with the wild-type AcNPV designated as "wtAcNPV"), as will be hereinafter more fully described. However, it should be understood that the invention is not limited to the particular recombinant baculovirus AcAaIT used to illustrate aspects of this invention, although AcAaIT is particularly preferred.

Therefore, the just described recombinant baculoviruses are one part, or aspect, of practicing this invention, while the pests treatable in accordance with the present invention are from the group insects, acarids, and nematodes. For example, illustrative insect pests that can be treated are the tobacco budworm, the cotton bollworm, the cotton leafworm, the spotted cutworm, the glassy cutworm, the bronzed cutworm, the fall armyworm, the beet armyworm, and the variegated cutworm. The other part, or aspect, of practicing this invention is using such already described recombinant baculoviruses in conjunction with chemical insecticides.

The synthetic, organic insecticides with which the present method may be practiced include: $Na^+$ channel agonists (i.e. pyrethroids), $Na^+$ channel blocking agents (i.e. pyrazolines), acetylcholinesterase inhibitors (i.e. organophosphates and carbamates), nicotinic acetylcholine binding agents (e.g. imidacloprid), gabaergic binding agents (e.g. emamectin and fipronil), octapamine agonists or antagonists (i.e. formamidines), and oxphos uncouplers (e.g. pyrrole insecticides).

As will be hereinafter further exemplified in the "Experimental" section, we have used low rates of cypermethrin (a Type II pyrethroid) or allethrin (a Type I pyrethroid) in combination with wild-type AcNPV (wtAcNPV) or AcAaIT (>$LCg_{99}$) in larvae of *H. virescens* to illustrate the invention.

The combination of the recombinant AcAaIT (even with low rates) of either pyrethroid noted above produced a dose-response greater than potentiation. Thus, use of AcAaIT in accordance with the invention in combination with allethrin or cypermethrin resulted in 54.8 and 64.6% reductions in the $LT_{50}s$, respectively, of the insect larvae when compared to wtAcNPV. These data illustrate a surprising property and an advantage for the invention. That is, pyrethroids and AaIT interact in a manner which magnifies the rate of kill beyond potentiation, and are synergizing (effect greater than the algebraic sum of the single effects) the rate of kill by AcAaIT. An even more surprising result is that the resistant strain of *H. virescens* is more sensitive to the recombinant baculovirus when compared with an insecticide-susceptible strain, demonstrating the potential utility of this invention.

We believe, without being bound by theory, that a simultaneous exposure of AaIT and pyrethroid results in a synergistic interaction at the sodium channel. It appears that the toxins that display synergistic activity in combination with recombinant baculovirus can be predicted based on the mechanism of action. As expected based on their activity as acetylcholinesterase inhibitors, organophosphates and carbamates were also found to be synergistic.

Thus, in practicing the invention, pests being controlled are treated (and/or their loci treated) with a combination of recombinant baculovirus and an organic insecticide predicted to be synergistic based on its mechanism of action. The combination may conveniently be applied for treating the pests as a single admixture.

As is well known, organic insecticides may be applied by means such as spraying, atomizing, dusting, scattering or pouring and may be formulated for such applications as powders, dusts, granulates, as well as encapsulations such as in polymer substances. When practicing this invention such conventional application means may be used. Preferably, the organic insecticide and recombinant baculovirus will be admixed in desired proportions, and may typically include inert carriers such as clay, lactose, defatted soy bean powder, and the like to assist in application.

However, it is possible to apply compositions including each component separately, by utilizing the baculovirus first then followed (preferably within about forty-eight hours) by the organic insecticide. When the baculovirus is first used (followed by organic insecticide), then the baculovirus can be applied by conventional means, such as spraying. An advantage of applying the baculovirus first is due to a "falling off" property described hereinafter in Example 3.

EXPERIMENTAL

Example 1

The recombinant AcAaIT that was used in performing experiments was constructed as recombinant transfer vector pAcUW2(B)·AaIT. This is orally infectious and expresses an insect-selective toxin (AaIT), which is isolated from the scorpion *Androctonus australis*, and is under the control of the p10 promoter. This construction was earlier reported in Bio/Technology, 9:848–852 (September 1991). Briefly, the AaIT toxin gene (sometimes also herein designated "AaHIT") in the transfer vector, pBK283, was digested with SacI and XbaI to excise the complete AaIT gene including a signal sequence of bombyxin required for secretion. The DNA fragment was inserted into the pTZ-18R plasmid between the SacI and XbaI sites. The plasmid was cleaved with SacI where a synthesized SacI-BamHI-SacI linker was inserted. The resulting plasmid contained two BamHI sites; one site near the 5' end of the toxin cDNA and the other site between the stop codon, and XbaI site of the original fragment. The insertion of the linker and AaIT gene was confirmed by 1% agarose gel electrophoresis by digestion with BamHI and screening for the resultant 300 base pair fragment. The protocol for GeneClean (BiolO1) was followed in order to isolate the toxin fragment for insertion in the transfer vector with approximately 30% recovery of the DNA fragment.

The excised AaIT gene fragment was ligated into the BglII cloning site of the digested and dephosphorylated plasmid vector pAcUW2(B), and then transformed in the JM 101 strain of E. coli. As a result of the ligation, both the BglII and BamHI sites were eliminated, and resultant plasmids were screened for a unique SacI site. Three SacI positive clones were identified from sixty colonies using 1% agarose gel electrophoresis. The direction of insertion was confirmed by double digestion with SacI (5' end of the AaIT gene) and BamHI (within the coding sequence of the polyhedrin gene of the transfer vector). Two of three recombinant transfer vectors were carrying the AaIT gene in the correct orientation and had the approximate 1.6 kbp fragment inductive of the correct orientation. The construction resulted in the AaIT cDNA sequence now inserted downstream of a duplicated p10 protein promoter and upstream of the polyhedrin gene 5 producing the recombinant plasmid pAcUW2(B)·AaIT.
Isolation of Recombinant ACNPV.

Spodoptera frugiperda cells (Sf-9) were propagated in ExCell 400 media (JR Scientific) supplemented with 2.5% fetal bovine serum. Sf-9 cells were cotransfected by calcium precipitation with the plasmid pAcUW2(B) and polyhedrin negative AcNPV DNA. Polyhedrin-infected cells were identified and collected at 5 days post infection. The recombinant virus was plaque purified by screening for the polyhedrin positive plaques. Purification of the recombinant virus was expedited by sodium dodecyl sulfate (SDS) treatment (1%) of the cells after each plaque purification in order to eliminate polyhedrin-negative, non-recombinant virus. After purification of the recombinant virus by the initial plaque assay, individual plaques were purified in 3 successive rounds, and the resultant, pure recombinants were propagated and stored at 4° C. and –80° C.
Screening the Recombinant AcUW2(B)·AaIT for Biological Activity.

After purification of the recombinant virus by the initial plaque assay, a total of six plaques were isolated and suspended in 500 $\mu$l of ExCell media with 2.5% fetal bovine serum. Sf-9 cells in 35 mm dishes (75% monolayer) were inoculated with 100 $\mu$L (~$10^6$ plaque forming units) of the suspension, and cells were collected 7 days post infection. The individual collections were centrifuged at 1000 g for 5 minutes, and the resulting supernatant was collected and separated from the pelleted cells. The cells were resuspended in double-distilled $H_2O$, treated with 1% SDS, then vortexed for 5 minutes and washed 3 times. Crude estimates of the plaque forming units per ml were determined from the supernatant.

Example 2

Detailed mortality studies were conducted with 2nd instar H. virescens larvae, as more fully described in the Experimental Protocol of the earlier cited paper (Bio/Technology, Vol. 9). Lethal times (LTs) were derived when 2nd instar H. virescens larvae were treated with the recombinant and wild-type ACNPV using a common dose of 250 polyhedrin inclusion bodies (PIBS) per plug of diet.

Table 1 shows the dose response and mortality times of second instar H. virescens larvae for treatments with AcUW2(B)·AaIT (AcAIT) and wild-type AcNPV.

TABLE 1

| Treatment | LD (PIBs) | | | LT (hours) | | |
| --- | --- | --- | --- | --- | --- | --- |
|  | 10 | 50 | 90 | 10 | 50 | 90 |
| AcUW2 (B) · AaIT | 1.56 | 13.3 | 113 | 59.8[a] | 88.0[a] | 129[a] |
| Wild-Type AcNPV | 2.72 | 21.9 | 175 | 91.4 | 125 | 172 |

[a]Significantly different from other treatments - POLO probit analysis program (C.I. 0.95)
PIBs = polyhedrin inclusion bodies
LT = lethal time;
LD = lethal dose These data demonstrate the ability of the AcUW2(B)·AaIT to kill H. virescens larvae significantly more quickly than the wild-type AcNPV.

Example 3

Larvae infected with the recombinant AcAaIT typically started showing symptoms of paralysis and stopped feeding 10 to 15 hours prior to death. As a result, these larvae can functionally be considered dead, and treatment with AcAaIT represents an approximately 40% reduction in the time required to kill host larvae when compared to wild-type AcNPV.

We designed experiments to assess the differences in feeding damage that would be incurred by tomato plants infested with larvae of H. virescens that had been infected with uninfected controls wild-type AcNPV or AcAaIT. Individual plants were infested with two 4th instar larvae that were uninfected (control, I) or had previously been infected with wild-type AcNPV (II) or /AcAaIT (III) 48 hours earlier. These larvae were allowed to feed continuously on the plants until death.

Figure 1:
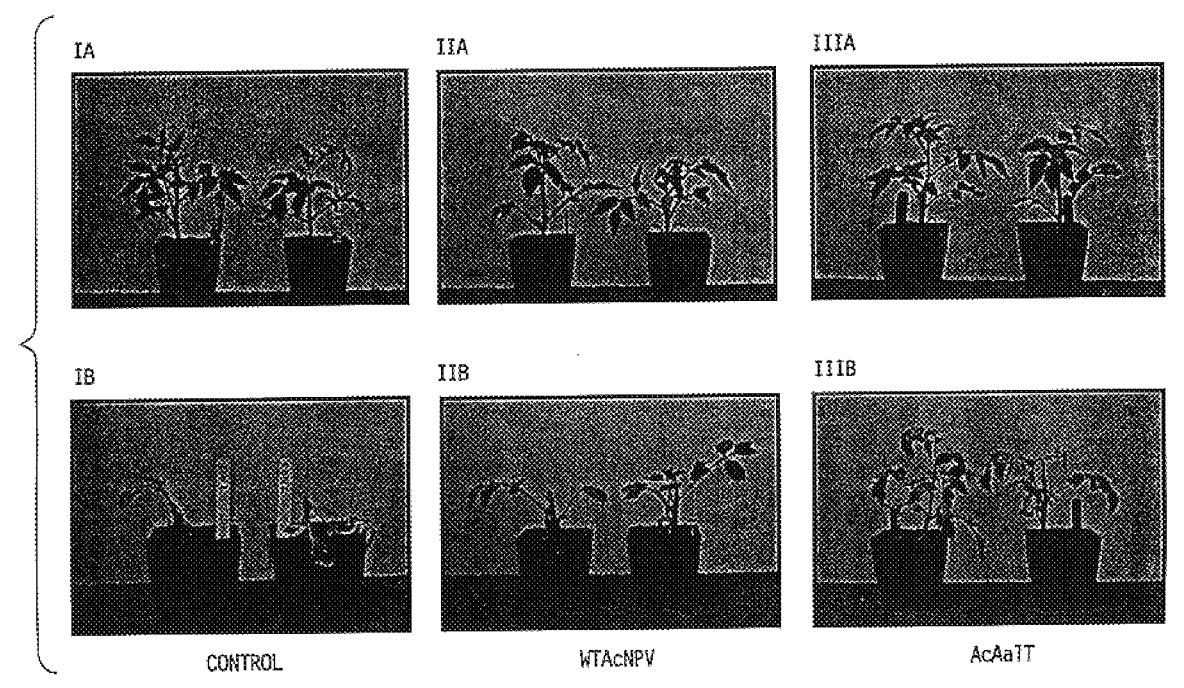

The AcAaIT treatment resulted in significantly less damaged plants. However, what is not evident is the fact that the larvae infected with AcAaIT were unable to inflict more damage on the tomato plants because they were falling from the plant. In fact, we observed five of eight 4th and 5th instar larvae infected with AcAaIT had fallen from the plant at 120 hours post infection. These individuals were apparently unable to crawl back up the plant due to the onset of paralysis and is sometimes referred to as the "falling off" property. This is illustrated by FIG. 1.

In FIG. 1, panels A illustrate the tomato plants before exposure to any larvae. Panel IA thus shows the control "before" larvae while panel IB shows the control after larvae without any virus had been freely feeding on the plant until the experiment was stopped. As demonstrated by the illustrations (reproduced from photographs), the control tomato plants were badly ravaged by the larvae. Turning to panel IIA, we again see tomato plants before introduction of larvae. In panel IIB larvae infected with wild-type AcNPV have been feeding on the plants for about 190–200 hours at which point the larvae had died and the experiment (for all panels IB, IIB, and IIIB) was stopped. While panel IIB showed considerable improvement over the panel IB control, the plant nevertheless had been subjected to up to about 200 hours of feeding activity before the larvae died. However, turning to panels IIIA (the beginning of the experiment) and IIIB (the end), we see that the panel IIIB plants have considerably more foliage when the experiment was stopped. These plants have more foliage because the inventive baculovirus AcAaIT infected larvae had their behavior disrupted before death so that five of eight larvae fell off the plant after 120 hours of feeding and the remaining three fell shortly thereafter.

Table 2 confirms that the insects become irritated and were not feeding on the food substrate or were wandering off the substrate a significant amount of time.

TABLE 2

Percentage of Time During Course of Infection
Tobacco Budworm Larvae Were Off the Food Substrate

| Food Substrate | AcAaIT | Wild Type Virus |
|---|---|---|
| Cotton | 80.40% | 13.30% |
| Romaine | 64.20% | 15.40% |
| Iceberg | 85.90% | 13.20% |
| Diet | 59.90% | 11.00% |

To obtain the data summarized by Table 2, the larvae were droplet fed virus at 2,000 PIBs/$\mu$l as neonates and checked every 6 to 8 hours. Larvae were scored as to whether they were off or on the food substrate as summarized in Table 2 above. At 64 hours post-infection, over 57% of all tobacco budworm larvae were not on the substrate, versus 32% of wild-type infected insects (which were not yet expressing symptoms). The purpose of this experiment was to confirm that larvae infected with AcAaIT before they die become paralyzed (or have their feeding behavior disrupted), while this does not happen with wild-type infected insects.

It is plausible that low levels of the neurotoxin, AaIT, early in the infection process may irritate the larval host, thus resulting in the "falling off" or eating disruption phenomena. Even though the larva is still potentially capable of feeding and causing damage, it no longer has access to the plant. With the reduced killing time and early immobilization of the host larva by paralysis, AcAaIT appears effectively to curtail food consumption which may translate into reduced feeding damage.

Example 4

The slow time to death and resulting crop damage is often cited as a major limitation to the commercial success of viral insecticides. Twenty-four to forty-eight hour mortality is a common target for classical insecticides. Thus, in this study we have concentrated on studying speed of kill expressed as lethal times ("LTs"). Analogous approaches can be used to determine lethal doses, which are likely to be of major economic importance.

As is summarized by Tables 3A and 3B, we investigated the interaction of low rates ($LC_{10}$–$LC_{20}$ at 24 h; Table 4) of six insecticides in combination with wild-type AcNPV or AcAaIT (>$LC_{99}$) in neonate larvae of H. virescens. For example, two of the compounds studied were pyrethroids, allethrin (Type I pyrethroid). In our study we found a subadditive response when low rates of allethrin or cypermethrin were combined with wild-type AcNPV. Thus, a combination of allethrin and wild-type AcNPV reduced the $LT_{50}$ to 71.9 h (53.8 h, theoretical additive effect), which is a 17.9% reduction when compared to wild-type ACNPV alone. Likewise, cypermethrin in combination with wild-type AcNPV produced a $LT_{50}$ of 65.8 h (52.1 h, theoretical), which represents a 24.2% reduction when compared to wild-type AcNPV. These results suggest that the pyrethroids and the wild-type AcNPV act independently of one another, but result in a subadditive response since the combination is positive although it is significantly less than a theoretical interaction (additive effect).

TABLE 3

Insecticides Combined with Wild-Type
and Recombinant Baculoviruses

| Compound | Common Name | Type | Mode of Action | Source |
|---|---|---|---|---|
| Allethrin | Cinerine, Alleviate, Bioallethrin | Pyrethroid Type I | Sodium Channel Agonist | Roussel Uclaf Div. Agrovetennaire, Paris, France |
| Cypermethrin | Ammo, Cymbush, Cynoff, Cyperkill, Fenom, Arrivo | Pyrethroid Type II | Sodium Channel Agonist | ICI Americas (Zeneca) Goldsboro, NC |
| DDT | DDT | Chlorinated Hydrocarbon | Sodium Channel Agonist | Synthesis by B. D. Hammock, UC Davis, CA |
| Endosulfan | Thiodan, Cyclodan, Thiosulfan, Malix, Thionex, Tiovel | Cyclodiene | GABA Channel Agonist | FMC Corp. Ag Chemical Group Middleport, NY |
| Methomyl | Lannate, Nudrin | Carbamate | AChE Inhibitor | E.I. DuPont de Nemours & Co. Wilmington, DE |
| Profenofos | Curacon, Polycron, Selecron | Organo-phosphate | AChE Inhibitor | Ciba-Geigy Greensboro, NC |

TABLE 3-continued

GABA, g-aminobutyric acid; AChE, acetylcholinesterase

Time-Response of Neonate Larvae of Tobacco Budworm to Recombinant or Wild-Type AcNPV with Low Concentrations of Classical Insecticides

| Treatment[a] | n | Slope ± SE | $LT_{10}$ (h: 95% CL) | $LT_{50}$ (h: 95% CL) | $LT_{90}$ (h: 95% CL) |
|---|---|---|---|---|---|
| WtAcNPV | 204 | 9.26 ± 0.41 | 64.9 (59.0–69.7) | 89.8 (85.0–93.4) | 123 (115–134) |
| AcAaIT | 276 | 7.73 ± 0.25 | 47.9 (44.8–50.6) | 70.2 (68.0–72.4) | 103 (98.3–109) |
| AcJHE.KK | 90 | 7.14 ± 0.53 | 50.5 (24.1–62.7) | 76.3 (60.8–99.7) | 115 (91.5–266) |
| Allethrin | 114 | 1.46 ± 0.19 | 17.3 (11.5–22.5) | 132 (106–185) | 1000 (552–2680) |
| Allethrin + AcAaIT | 125 | 3.54 ± 0.20 | 17.5 (12.6–21.7) | 40.2 (34.9–45.5) | 92.5 (78.2–118) |
| Allethrin + WtAcNPV | 119 | 2.31 ± 0.19 | 20.0 (16.1–23.5) | 71.9 (65.5–80.0) | 258 (205–354) |
| Cypermethrin | 110 | 1.49 ± 0.24 | 17.1 (7.99–24.8) | 124 (97.5–195) | 902 (436–4190) |
| Cypermethrin + AcAaIT | 112 | 3.19 ± 0.27 | 12.5 (5.60–18.5) | 31.5 (22.7–38.1) | 79.0 (65.3–111) |
| Cypermethrin + WtAcNPV | 109 | 2.09 ± 0.23 | 16.0 (10.9–20.7) | 65.8 (59.3–73.8) | 270 (203–418) |
| Cypermethrin + AcJHE.KK | 83 | 3.81 ± 0.27 | 24.2 (18.7–28.8) | 52.5 (47.3–58.0) | 114 (97.8–142) |
| DDT | 80 | 1.45 ± 0.30 | 12.6 (3.90–23.8) | 96.7 (73.5–165) | 740 (318–10320) |
| DDT + AcAaIT | 80 | 3.12 ± 0.32 | 16.0 (7.84–23.0) | 41.2 (31.4–48.7) | 107 (84.6–160) |
| DDT + WtAcNPV | 80 | 2.25 ± 0.29 | 17.7 (5.78–28.2) | 66.0 (49.9–84.6) | 245 (159–688) |
| Endosulfan | 80 | 1.51 ± 0.27 | 10.4 (3.75–17.3) | 73.3 (61.0–90.3) | 514 (296–1580) |
| Endosulfan + AcAaIT | 80 | 4.23 ± 0.35 | 23.8 (16.5–29.7) | 47.7 (40.6–54.2) | 95.4 (81.6–121) |
| Endosulfan + WtAcNPV | 80 | 2.57 ± 0.30 | 24.7 (14.5–33.0) | 78.1 (66.7–93.6) | 247 (176–460) |
| Methomyl | 125 | 0.69 ± 0.20 | 4.84 (0.12–13.1) | 358 (182–4070) | 26563 (2870–1.25 × $10^8$) |
| Methomyl + AcAaIT | 125 | 3.27 ± 0.28 | 13.7 (9.16–17.8) | 34.3 (29.2–38.8) | 85.7 (73.3–108) |
| Methomyl + WtAcNPV | 125 | 2.37 ± 0.22 | 14.6 (8.34–20.2) | 50.3 (42.5–58.1) | 173 (132–276) |
| Profenofos | 150 | 0.76 ± 0.19 | 8.10 (2.61–17.5) | 401 (260–676) | 19810 (9472–1.88 × $10^4$) |
| Profenofos + AcAaIT | 150 | 3.81 ± 0.23 | 24.5 (20.3–28.2) | 53.2 (49.2–57.1) | 115 (103–133) |
| Profenofos WtAcNPV | 150 | 2.33 ± 0.19 | 16.5 (10.8–21.6) | 58.5 (52.0–65.2) | 208 (163–302) |

[a]Dose-response curves were developed for the classical insecticides using neonate larvae of *H. virescens*. Neonate larvae infected with NPVs were exposed to 2000 polyhedrin inclusion bodies (PIbs; ≥ $LC_{99}$) using a droplet feeding assay. Three NPVs were utilized including wtAcNPV, AcAaIT, and acJHE.KK. Larvae which were to be combined with an insecticide were immediately transferred to vials treated with a $LC_{10}$—$LC_{20}$ (24 h) of the insecticide. Mortality was recorded at 8 to 12 h intervals, and the data were anlyzed using a log-probit analyses program (POLO-PC).

However, as shown by the data of Table 5, the combination of the recombinant AcAaIT with low rates of either pyrethroid produced a dose-response greater than an additive response. Thus, we observed that AcAaIT in combination with allethrin or cypermethrin resulted in 30.0 and 38.7% reductions in the $LT_{50}$s, respectively, when compared to AcAaIT alone. The $LT_{50}$S for the combination of AcAaIT and allethrin or cypermethrin were 40.2 h and 31.5 h post infection, respectively (Table 3). Both of these $LT_{50}$S are lower than the theoretical (additive effect) $LT_{50}$s of 45.8 h and 44.8 h post infection, respectively. These data suggest that the pyrethroids and AaIT interacted in a manner, which magnifies the rate of kill beyond potentiation and are synergizing (supplemental synergism—quicker effect than the algebraic sum of the single effects) the rate of kill by AcAaIT.

Another recombinant virus, AcJHE.KK, was used as a control for the recombinant NPV, AcAaIT. AcJHE.KK expresses a modified version of juvenile hormone esterase, an insect-derived enzyme important in the regulatory development of many lepidopterous insects. The modified JHE has been shown to be insecticidal to several lepidopterous insects (Bonning and Hammock, 1994). Although the mode of action of JHE.KK is not yet fully understood, we can assume it does not interfere with the nervous system of insects. We found a 23.8% reduction in the $LT_{50}$ when AcJHE.KK was combined with cypermethrin. The $LT_{50}$ for this combination was 52.5 h which is significantly higher than 47.2 h predicted for the theoretical combination and indicates a subadditive not a supplemental effect (Table 5). Since AcJHE.KK has a $LT_{50}$ similar to that of AcAaIT these data indicate that the pyrethroids do not synergize indiscriminately any baculovirus with enhanced speed of kill. Thus, these data provide further support for a supplemental synergistic relationship between the recombinant virus, AcAaIT, and pyrethroid insecticides.

As further shown by Table 3B, another sodium channel agonist, DDT, was also screened for interactions with the NPVs. A combination of DDT and wild-type AcNPV resulted in a 24% reduction in the $LT_{50}$ (66.0 h) when compared to wild-type AcNPV alone (Table 3B). Our data indicate that this combination produced a subadditive effect (46.7 h, theoretical). DDT combined with AcAaIT resulted in a 29.0% reduction in the $LT_{50}$ (41.2 h) when compared to AcAaIT alone. The results of this combination suggest a purely additive response (theoretical actual) since the theoretical time has a very similar $LT_{50}$ of 40.8 hours.

Yet another insecticide, endosulfan (a cyclodiene), was also combined with the NPVs to explore any interactions. Interestingly, our data indicate an antagonistic interaction when endosulfan was combined with the wild-type AcNPV. The $LT_{50}$ for the combination was 78.1 h which was later than the 73.3 h produced by the insecticide alone indicating an antagonistic response. However, the combination of AcAaIT with endosulfan resulted in an $LT_{50}$ of 47.7 h, which is significantly quicker than either AcAaIT or endosulfan alone and indicates a subadditive response.

Yet additional studies were performed with a carbamate (methomyl) or an organophosphate (profenofos) insecticide in combination with AcNPV or AcAaIT. Interestingly, both insecticide and wild-type AcNPV combinations resulted in supplemental synergism. The derived $LT_{50}$ for methomyl and wild-type AcNPV was 50.3 h compared to 71.9 h for the theoretical response (Table 3). Likewise, profenofos in combination with wild-type AcNPV resulted in a $LT_{50}$ of 58.5 h versus 73.5 h for the theoretical additive response. Similarly, the combinations of methomyl or profenofos with AcAaIT resulted in supplemental synergistic responses. The $LT_{50}$s for methomyl or profenofos with AcAaIT were 34.3 h and 53.2 h, respectively. The combination of AcAaIT and methomyl show a 61.8% quicker rate of kill than wild-type AcNPV alone, and a 36.0% quicker rate than AcAaIT alone. Profenofos and AcAaIT result in a 40.8 and 17.0% reduction in time of kill compared to wild-type AcNPV and AcAaIT, respectively.

Overall, our data indicate that the pyrethroid insecticides and ACHE inhibitors appear to provide the greatest chance of synergizing the recombinant virus, AcAaIT, in the field and for this reason, use of the recombinant AcAaIT is particularly preferred. However, other recombinant strains of baculovirus expressing the AaIT gene would be also preferred (i.e. HzAaIT or SfAaIT). For the pyrethroids these data suggest that a simultaneous exposure of AaIT and pyrethroid may result in a synergistic interaction at the insect sodium channel. Based on these results, varying rates of pyrethroids in combination with AcAaIT or other recombinant viruses expressing AaIT should be tested for efficacy in the field. The low rates of pyrethroids we are suggesting should have minimal effect on beneficial arthropods, thus not compromising the host specificity provided by the virus. The combination is believed also useful in resistance management strategies.

Both carbamate and organophosphate insecticides act as poisons at the peripheral nervous system. These compounds inhibit the enzyme, acetylcholinesterase, resulting in an accumulation of acetylcholine in the synapse regions of nerves. This accumulation of acetylcholine produces a plethora of neurological responses resulting in a paralysis of the insect. Therefore, it could be suggested that the simultaneous action of the insecticide and the peptide toxin would result in a supplemental synergistic response. It is difficult to account for the contribution, if any, made by the virus itself. However, NPVs can infect nerve cells, and eventually the infection results in lysis of the cell. One could envision that the lysis of nerve cells by NPV infection would result in an increase of neurotransmitters in the peripheral nervous system which could lead to neuromuscular abnormalities. This action might account for the supplemental synergism observed with both wild-type and recombinant NPVs when combined with methomyl or profenofos.

As indicated previously, these studies have emphasized the effects of combinations of viral and chemical insecticides on $LT_{50}$, but the same approaches could be applied to dose as well as time. We used here approximate $LD_{10}$s (24 h) of the pesticides reported here to minimize the symptomology and mortality resulting directly from the chemical pesticide (Table 4). In practice a variety of factors would influence the rates used, including the cost and availability of the biological and chemical pesticide, environmental concerns, level of resistant populations in the field, and other pest management considerations.

Example 5

In this study we compared the LTs of wild-type and AcAaIT against pyrethroid-susceptible and -resistant (PEG) larvae of H. virescens. The response (LTs) of the susceptible and PEG neonate larvae to wild-type AcNPV and AcAaIT were very comparable. Statistical analysis (POLO-PC) of the data indicated no significant difference in the slopes (PEG=9.51, susceptible=9.82, 95% CL) or intercepts. However, when these viruses were tested for effectiveness against pyrethroid-resistant larvae our results lead to the surprising results as follows. Analysis of the data indicated a significant difference between the slopes (PEG=13.9, susceptible=7.73, 95% CL) and intercepts for wild-type and AcAaIT, but our results indicated that the resistant strain, not the susceptible strain, was killed in a more timely manner. The $LT_{90}$ for the Stoneville strain was 103 h post infection versus 78.1 h for the PEG strain representing a highly significant 24.1% quicker rate of kill against the resistant strain.

These results indicate that a recombinant baculovirus such as AcAaIT may be more effective against pyrethroid-resistant larvae than pyrethroid-susceptible larvae of H. virescens in field situations and could be used as an effective agent to combat pyrethroid resistance.

Thus, one aspect of the invention is use of AcAaIT to control outbreaks of pest insects resistant to pyrethroids. Furthermore, AcAaIT could be integrated into a resistance management strategy to delay or prevent pyrethroid resistance in the field. In addition to reducing resistant populations, this strategy should extend the efficacy of the pyrethroid insecticides.

Example 6

We investigated the interaction of low rates ($LC_{10}$–$LC_{20}$ at 24 h, Table 4) of several insecticides in combination with wild-type AcNPV or AcAaIT (>$LC_{99}$) in neonate larvae of H. virescens. Two of the compounds studied were pyrethroids, allethrin (Type I pyrethroid) or cypermethrin (Type II pyrethroid). In our study we found a subadditive response when low rates of allethrin or cypermethrin were combined with wild-type AcNPV.

TABLE 4

| Compound | n | μg Insecticide/Vial | % Mortality at 24 hours |
|---|---|---|---|
| Allethrin | 121 | 0.05 | 14.0 |
| Cypermethrin | 110 | 0.008 | 11.8 |
| DDT | 80 | 0.02 | 18.8 |
| Endosulfan | 80 | 0.002 | 17.5 |
| Methomyl | 125 | 0.02 | 20.8 |
| Profenofos | 150 | 0.06 | 16.3 |

Lethal concentrations of insecticides ($LC_{10}$–$LC_{20}$) were chosen based on results from Campanhola & Plapp (1989).

Referring to Table 5 below, a combination of allethrin and wild-type AcNPV reduced the $LT_{50}$ to 71.9 h (53.1 h, theoretical additive effect) which is a 17.9% reduction when compared to wild-type AcNPV alone. Likewise, cypermethrin in combination with wild-type AcNPV produced a $LT_{50}$ of 65.8 h (52.1 h, theoretical) which represents a 24.2% reduction when compared to wild-type AcNPV. These results suggest that the pyrethroids and the wild-type AcNPV act independently of one another but result in a subadditive response since the combination is positive although it is significantly less than a theoretical interaction (additive effect).

The combination of the recombinant NPV, AcAaIT, with low rates of either pyrethroid produced a dose-response greater than an additive response. We observed that AcAaIT in combination with allethrin or cypermethrin resulted in 30.0 and 38.7% reductions in the $LT_{50}$s, respectively, when compared to AcAaIT alone. The $LT_{50}$s for the combination of AcAaIT and allethrin or cypermethrin were 40.2 h and 31.5 h. post infection, respectively (Table 5). Both of these $LT_{50}$s are lower than the theoretical (additive effect) $LT_{50}$s of 45.8 h and 47.2 h post infection, respectively. These data illustrate the synergistic effect.

neurotoxin in said insect pests treated therewith, and a pyrethroid insecticide, wherein said treating is sufficient to (i) infect said insect pests with the genetically engineered insect virus so as to express said insecticidal neurotoxin in said insect pests and (ii) contact said insect pests with the pyrethroid insecticide;

wherein the combination is effective to increase the speed of pest killing with respect to pest killing speed for insect pests either infected with the insect virus alone or contacted with the pyrethroid insecticide a lone.

2. The method of claim 1, wherein the insecticidal neurotoxin is an arthropod toxin.

3. The method of claim 1, wherein the insecticidal neurotoxin is from a scorpion, wasp, snail, or spider.

TABLE 5

Interactions of Recombinant or Wild-Type AcNPV with Low Concentrations of Classical Insecticides

| Treatment[a] | Actual Kill Time ($LT_{50}$, h) | Theoretical Kill Time (h)[b] | % Reduction from WtAcNPV | % Reduction from RecNPV | Effect[c] |
|---|---|---|---|---|---|
| AcAaIT | 70.2 | — | 21.8 | — | — |
| WtAcNPV | 89.8 | — | — | — | — |
| AcJHE.KK | 76.2 | — | 15.0 | — | — |
| Allethrin | 132 | — | — | — | — |
| Allethrin + AcAaIT | 40.2 | 45.8 | 55.2 | 30.0 | Supplemental |
| Allethrin + WtAcNPV | 71.9 | 53.8 | 17.9 | — | Subadditive |
| Cypermethrin | 124 | — | — | — | — |
| Cypermethrin + AcAaIT | 31.5 | 44.8 | 64.9 | 38.7 | Supplemental |
| Cypermethrin + WtAcNPV | 65.8 | 52.1 | 24.2 | — | Subadditive |
| Cypermethrin + AcJHE.KK | 52.5 | 47.2 | 41.2 | 23.8 | Subadditive |
| DDT | 96.7 | — | — | — | — |
| DDT + AcAaIT | 41.2 | 40.8 | 54.1 | 29.0 | Additive |
| DDT + WtAcNPV | 66.0 | 46.7 | 24.0 | — | Subadditive |
| Endosulfan | 73.3 | — | — | — | — |
| Endosulfan + AcAaIT | 47.7 | 36.0 | 46.9 | 22.6 | Subadditive |
| Endosulfan + WtAcNPV | 78.1 | 40.7 | 11.9 | — | Antagonism |
| Methamyl | 358 | — | — | — | — |
| Methamyl + AcAaIT | 34.3 | 59.5 | 61.8 | 36.0 | Supplemental |
| Methamyl + WtAcNPV | 50.3 | 71.9 | 39.5 | — | Supplemental |
| Profenofos | 401 | — | — | — | — |
| Profenofos + AcAaIT | 53.2 | 59.9 | 40.8 | 17.0 | Supplemental |
| Profenofos + WtAcNPV | 58.5 | 73.5 | 31.3 | — | Supplemental |

LT = lethal time; RecNPV = Recombinant NPV.
[a]Dose-response curves were developed for the classical insecticides using neonate larvae of *H. virescens*. Larvae infected with NPVs were exposed to 2000 polyhedrin inclusion bodies (PIBs; ≥ $LC_{99}$) using a droplet feeding assay. Larvae were immediately transferred to vials treated with an approximate $LC_{10}$—$LC_{20}$ (24 h) of the insecticide and scored every 8 to 12 h.
[b]Theoretical Kill Time = 1 ÷ [Reciprocal of $LT_{50}$ for virus alone + Reciprocal of $LT_{50}$ for insecticide alone].
[c]Effect - Supplemental synergism is Actual Time < Theoretical Time; Additive synergism is Actual Time ≈ Theoretical Time; Subadditive Synergism is Actual Time > Theoretcial Time and Actual Time < Fastest Time Alone; Antagonism is Actual Time > Fastest Time Alone.

The foregoing examples illustrate certain embodiments of the present invention, and are not intended to limit the scope of the invention, which is defined in the appended claims.

What is claimed is:

1. A method for killing insect pests comprising:

treating said insect pests with a combination of a genetically engineered insect virus from Autographa californica or Heliothis armigera expressing an insecticidal 4. A method for killing insect pests, which are resistant to pyrethroid insecticide, comprising:

treating said insect pests with a genetically engineered insect virus expressing an insecticidal neurotoxin in said insect pests treated therewith, wherein the genetically engineered insect virus is an *Autographa californica* nuclear polyhedrosis virus, and wherein said treating is sufficient to infect said insect pests with the genetically engineered insect virus and the insecticidal neurotoxin is expressed in said insect pests.

5. The method of claim 4, wherein the speed of kill is faster for said resistant pests than for nonresistant insect pests.

6. Th e method of claim 4, wherein said treating of the insect pests with the insect virus is effective to cause feeding behavior disruption in a insect pest population containing said insect pests, wherein the insect population is treated prior to killing.

7. An insecticidal composition comprising:
  (a) a genetically engineered insect virus which contains an inserted gene that encodes an insecticidal neurotoxin, wherein said insecticidal neurotoxin is expressed in an insect pest when said insect pest is infected with the insect virus and wherein the genetically engineered insect virus is an *Autographa californica* nuclear polyhedrosis virus, and
  (b) a pyrethroid insecticide,
    wherein when (a) and (b) are both administered to an insect pest, the combination is effective to decrease a median lethal time for said insect pest with respect to a median lethal time with either (a) or (b) alone.

8. The insecticidal composition of claim 7, wherein the insecticidal neurotoxin is an anthropod toxin.

9. The insecticidal composition of claim 7, wherein the insecticidal neurotoxin is from a scorpion, wasp, snail, or spider.

10. The insecticidal composition of claim 7, wherein the insecticidal neurotoxin is from *Androctomus australis*.

11. The insecticidal composition of claim 7, wherein (a) and (b) are an admixture.

12. A method to delay or inhibit pyrethroid insecticide resistance of an insect pest in a field, comprising:

Applying a genetically engineered *Autographa californica* or *Heliothis armigera* insect virus expressing an insecticidal neurotoxin to the insect pest that is resistant to a pyrethroid insecticide.

13. The method of claim 12, wherein the genetically engineered insect virus provides a quicker rate of kill against the resistant insect pest than an amount of the pyrethroid insecticide alone.

* * * * *